United States Patent [19]

Confalone et al.

[11] 4,062,868

[45] Dec. 13, 1977

[54] SYNTHESIS OF BIOTIN

[75] Inventors: Pasquale Nicholas Confalone; Elizabeth Dianne Lollar, both of Bloomfield; Giacomo Pizzolato, Belleville; Milan Radoje Uskokovic, Upper Montclair, all of N.J.

[73] Assignee: Hoffmann-La Roche Inc., Nutley, N.J.

[21] Appl. No.: 771,218

[22] Filed: Feb. 23, 1977

[51] Int. Cl.$^2$ .................. C07D 333/24; A01N 9/22; A01N 9/00

[52] U.S. Cl. .................. 260/332.2 A; 544/95; 260/307 F; 260/307 FA; 260/329 S; 260/332.3 P; 260/332.5; 260/609 R; 424/273 R; 424/275; 548/303

[58] Field of Search .................. 260/332.2 A

[56] References Cited

U.S. PATENT DOCUMENTS 3,979,396  9/1976  Confalone .................. 260/332.2 A Primary Examiner—Alan M. Siegel
Attorney, Agent, or Firm—Samuel L. Welt; Bernard S. Leon; Richard A. Gaither

[57] ABSTRACT

A novel process for the preparation of biotin is disclosed wherein said process employs inexpensive starting materials and reagents resulting in the obtention of biotin devoid of the biologically inactive stereoisomers.

3 Claims, No Drawings

SYNTHESIS OF BIOTIN

BACKGROUND OF THE INVENTION

Biotin, vitamin H, is a natural product found largely in the kidney, liver, egg yolk, milk and yeast. The compound is used to prevent symptoms of eggwhite injury in experimental animals. Its prime medical use is in various dermatitides.

Biotin has been prepared synthetically by Harris et al. (Science, 97, 447 (1943) and Baker et al. (J. Org. Chem. 12, 167 (1947), among others. None of these syntheses, however, were commercially feasible. The first commercial synthesis of biotin resulted from the work of Goldberg and Sternbach (U.S. Pat. Nos. 2,489,235 and 2,489,236).

Many previous biotin syntheses suffer from the disadvantage that stereoisomeric mixtures of intermediates leading to biotin stereoisomers are formed, thus requiring costly and time consuming separations. These separations also lead to decreased yields of biotin. In the instant invention an inexpensive and readily available starting material, i.e., a 3-halocycloheptene, preferably 3-bromocycloheptene, is converted to biotin in a stereospecific synthesis, resulting in the obtention of biotin devoid of biologically inactive stereoisomers.

According to the instant invention, biotin is obtained from a relatively inexpensive starting material, in a stereospecific fashion thus avoiding the costly and inefficient chemical separations heretofore required.

SUMMARY OF THE INVENTION

This invention is directed to a process for selectively synthesizing biotin, which has the structural formula:

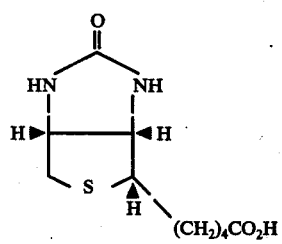

from a 3-halocycloheptene, a compound of the formula:

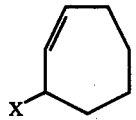

wherein X is halogen.

DETAILED DESCRIPTION OF THE INVENTION

As used throughout this application, the term "lower alkyl" denotes straight chain and branched chain saturated aliphatic hydrocarbon groups having from 1 to 8 carbon atoms, such as methyl, ethyl and propyl, preferably methyl. As also used herein, the term "aryl" signifies mononuclear aromatic hydrocarbyl groups of 6 to 13 carbon atoms, such as phenyl and tolyl, which can be unsubstituted or substituted in one or more positions with a lower alkylenedioxy, a halogen, a nitro, a lower alkyl or a lower alkoxy substituent, and polynuclear aryl groups of 10 to 17 carbon atoms, such as naphthyl, anthryl, phenanthryl and azulyl, which can be substituted with one or more of the aforementioned groups. The preferred aryl groups are the substituted and unsubstituted mononuclear aryl groups, particularly phenyl. As further used herein, the term "aryl lower alkyl" comprehends groups wherein aryl and lower alkyl are as defined above, particularly benzyl. As still further used herein, the term "lower alkoxy" comprehends groups having from 1 to 7 carbon atoms such as methoxy and ethoxy. Also herein, the term "halogen" or "halo", unless otherwise stated, comprehends fluorine, chlorine, bromine and iodine. Further herein, the term "lower alkylenedioxy" comprehends lower alkylenedioxy groups having 1 to 4 carbon atoms, such as methylenedioxy and ethylenedioxy. The term "alkali metal" as used herein, unless otherwise stated, denotes sodium, lithium, and potassium. The term "alkaline earth metal" denotes calcium, magnesium, and barium. The term "lower acyl" as used herein, denotes acyl groups having 1–8 carbon atoms (including the carbonyl carbon). As still further used throughout this application, in the pictorial representations of the compounds of this application, a thickened tapered line ◄ indicates a substituent which is in the β-orientation (above the plane of the molecule), a dotted line ---- indicates a substituent which is in the α/orientation (below the plane of the molecule) and a wavy line ⁓ indicates a substituent which is in either the α- or β-orientation. It is to be understood that the pictorial representations of the compounds given throughout the specification are set forth for convenience and are to be construed as inclusive of other forms, including enantiomers and racemates, and are not to be construed as limited to the particular form shown. A black dot ● indicates the configuration of the hydrogen atom at that stereocenter to be in the β-orientation.

In accordance with this invention, biotin is obtained by first converting haloclohepetene of formula I to a compound of the formula:

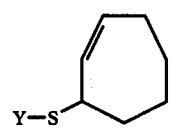

wherein Y is a lower acyl moiety derived from the thiolacid employed in the preparation of compound II.

The transformation of compound I to compound II occurs by way of an alkylation between compound I and a thiolacid, preferably thiolacetic acid. The aforementioned alkylation is carried out in a polar protic or aprotic solvent in the presence of a base. Typical solvents that may be employed in this reaction are acetonitrite, benzonitrile, chlorobenzene, methylenechloride, chloroform, aniline, pyridine, acetone, lower alkanols, nitrobenzene, dimethylformamide (DMF), dimethylsulfoxide (DMSO) hexamethylphosphoric acid triamide, and the like.

In carrying out the above reaction, any conventional nitrogen containing base may be employed. Typical of these bases are primary amines such as methyl, or ethyl amines, aniline; secondary amines such as dimethyl, diethyl amines, pyrrole; tertiary amines such as trimethyl, triethylamines and pyridine. Inorganic bases such as alkali metal hydroxides, alkaline earth metal hydroxides and alkali metal alkoxides may also be employed. Although temperature and pressure are not critical, the reaction is usually carried out at atmospheric pressure and at a temperature ranging from about −20° C to about 50° C., preferably at about room temperature.

Compound II is then transformed to a compound of the formula:

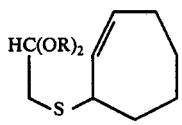

III wherein R is lower alkyl.

The conversion of compound II to compound III occurs by reacting compound II with a halogenated acetal of the formula:

wherein X and R are as defined above; in the presence of an alkali metal alkoxide.

The transformation of compound II to compound III takes place at a temperature of from about 50° C. to the reflux temperature of the solvent. The solvent employed may be an inert solvent such as a lower alkanol, e.g., methanol, ethanol and the like, diloweralkyl ethers such as diethyl ether, dibutyl ether, and the like, cyclic ethers, such as dioxane and tetrahydrofuran. Solvents such as cyclohexane, benzene, toluene, xylene, pentane, heptane, hexane and the like. The alkali metal alkoxide employed is preferably sodium ethoxide.

Compound III is then hydrolyzed to a compound of the formula:

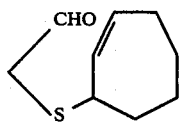

IV

Any conventional method of preparing an aldehyde from an acetal may be used to convert the compound of formula III to formula IV. Preferably, compound III is acid hydrolyzed in the presence of an aqueous co-solvent and a strong acid. Typical aqueous co-solvents may consist of dilower alkyl ketones such as acetone, methyl ethyl ketone and the like with water and also lower alkanols and water. Typical strong acids that may be employed are sulfuric, phosphoric, hydrochloric, p-toluenesulfonic and methane sulfonic acids. The reaction is generally carried out at atmospheric pressure and at the reflux temperature of the solvent.

Compound IV is then transformed to a compound of the formula:

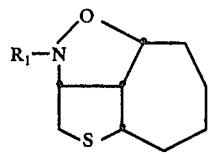

V wherein $R_1$ is aryl lower alkyl.

The transformation of compound IV to compound V proceeds by way of a 1,3-intramolecular dipolar addition. This transformation proceeds by treating compound IV with an aryl lower alkyl hydroxylamine, preferably benzylhydroxylamine in the presence of a polar aprotic solvent and a catalytic amount of an amine base. The amine bases and polar aprotic solvents may be selected from those set forth hereinabove. Particularly preferred solvents are acetonitrile and methylene chloride. The transformation of compound IV to compound V is particularly unique in that there is provided a tricyclic system containing all three stereocenters of biotin in their correct relative configuration. The conversion of compound IV to compound V is generally carried out at atmospheric pressure and at the reflux temperature of the solvent. This reaction is stereospecific and no other stereoisomer of V is produced.

Compound V is then converted to a compound of the formula:

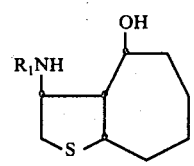

VI wherein $R_1$ is as previously defined.

The above transformation is accomplished by reduction of compound V employing conventional reducing agents such as Al/Hg in methanol, alkali metal borohydrides, such as sodium and lithium borohydrides, zinc, metal, iron and stannous chlorides in the presence of strong acids. Typical strong acids such as HCl, HBr, HI, $H_2SO_4$, $HNO_3$, $H_3PO_4$, chloroacetic, trichloroacetic acid and the like. In addition, and particularly preferred, as reducing agents are $LiAlH_4$ diisobutylaluminum hydride (DIBAL) and Zn metal in the presence of an admixture of water and acetic acid. Alternatively, the foregoing reduction may be accomplished using conventional hydrogenation catalysts such as platinum, palladium, Raney nickel and Raney cobalt. These catalysts may be supported or unsupported. A particularly preferred hydrogenation catalyst is palladium on a carbon support. The reduction of compound V to VI may be carried out in either an inert organic solvent (such as those previously mentioned herein) or the above-mentioned aqueous co-solvents at temperatures ranging from room temperature to the reflux temperature of the solvent.

Compound VI is then converted to a compound of the formula:

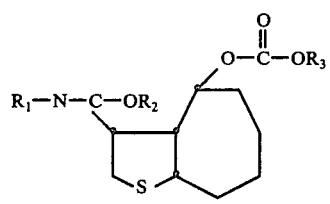

VII wherein $R_2$ and $R_3$ are lower alkyl, and $R_1$ is as defined above; by treating compound VI with at least two equivalents of a hydrocarbon substituted haloformate. Two equivalents of the hydrocarbon substituted haloformates are required in order to avoid the obtention of undesirable by-products. Use of less than two equivalents results in the obtention of a mixture of starting material VI, N-acylated and O-acylated products. Typical hydrocarbon substituted haloformates that may be used are methyl, ethyl and isopropyl chloroformates. Other hydrocarbon substituted chloroformates that may be used are phenyl and benzyl chloroformates. The conversion is generally carried out in a lower alkanol/water/inorganic base mixture. Typical lower alkanols are methanol, ethanol and the like. Typical inorganic bases are sodium and potassium bicarbonate, sodium and potassium hydroxide, ammonium hydroxide and the like. Particularly preferred is methylchloroformate in an admixture of methanol-aqueous sodium bicarbonate.

Compound VII is then converted to a compound of the formula:

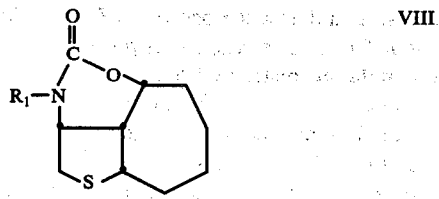

VIII wherein $R_1$ is as previously defined; by treating compound VII with an alkali or alkaline earth metal hydroxide in an aqueous/lower alkanol co-solvent. The reaction is generally carried out at atmospheric pressure under reflux conditions.

Compound VIII is subsequently transformed to a compound of the formula:

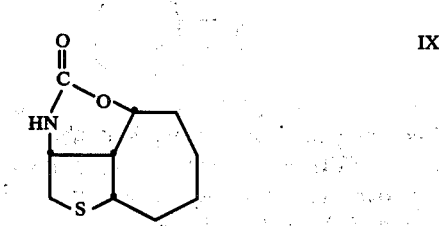

IX by treating the former compound with an alkali metal in the presence of an organic nitrogen base. The organic nitrogen bases may be selected from those mentioned hereinbefore and ammonia. Particularly preferred reagents for this transformation are sodium, potassium, or lithium metal in the presence of ammonia or lower alkyl primary amines.

Compound IX is then base-hydrolyzed to form a compound of the formula:

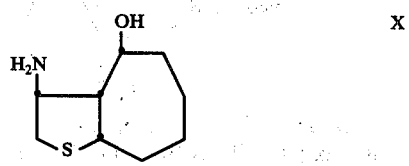

X

The hydrolysis of compound IX to compound X is accomplished by conventional basic hydrolysis techniques. Typical bases that may be employed are those mentioned hereinbefore. Particularly preferred are the alkali and alkaline earth metal hydroxides. The hydrolysis is carried out at atmospheric pressure and under reflux conditions.

Compound X is then transformed to a compound of the formula:

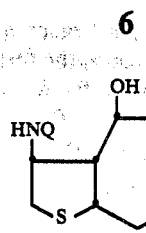

XI wherein Q is a conventional nitrogen protecting group. Typical of the protecting groups that may be employed are —$CO_2R_4$, —$COR_4$, tosyl,—$CO_2$-t-butyl and —$COCX'_3$, wherein $R_4$ is lower alkyl and X is as defined hereinbefore.

Compound XI may be formed by reacting compound X with the corresponding lower alkyl or aryl lower alkyl monocarboxylic acid anhydrides and acid halides from which Q is derived. Another compound that may be used to protect the amino group is t-butyl carbonylazide. Q may also be derived from lower alkyl haloformates. The reaction generally takes place in a lower alkanol. A particularly preferred reaction medium is methylchloroformate in methanol. The reaction is generally conducted at room temperature and at atmospheric pressure. The foregoing list of protective groups is merely illustrative and is not intended to be exhaustive. Any conventional amino protective group may be employed to form compound XI.

Compound XI is then transformed into a compound of the formula:

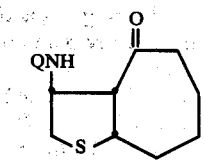

XII wherein Q is as defined above; by treating compound XI with DMSO in the presence of a monocarboxylic acid anhydride, preferably acetic anhydride or trifluoroacetic anhydride. It is necessary that this combination of reagents be employed to insure that oxidation is limited to the hydroxy group of compound XI.

Compound XII is then transformed to a compound of the formula:

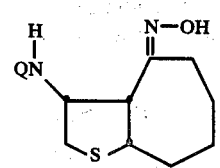

XIII wherein Q is as defined above.

Compound XIII can be obtained from compound XII by any conventional method of preparing an oxime from a keto compound. Conventionally, compound XII may be treated with a hydroxylamine hydrohalide, preferably hydroxylamine hydrochloride in a nitrogen containing base. The preferred nitrogen bases are amines, which may be selected from any of those mentioned hereinbefore. The reaction may be carried out at atmospheric pressure and room temperature. Further, this reaction may be carried out in an inert organic solvent. Typical inert organic solvents are any of those mentioned hereinbefore, particularly ether or methanol.

Compound XIII then undergoes a Beckman rearrangement to form a lactam of the formula:

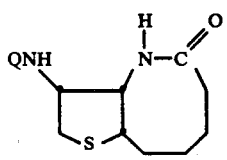

XIV wherein Q is as previously defined.

Compound XIV is obtained by treating compound XIII with a strong acid. Typical strong acids that may be employed are those mentioned hereinbefore. A particularly preferred strong acid is polyphosphoric acid. This rearrangement is generally carried out at atmospheric pressure and temperatures of from about 75° C. to about 125° C.

The lactam of formula XIV may be converted to compounds of the formula:

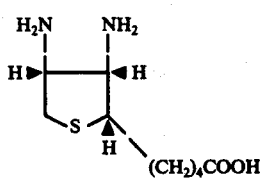

XV by procedures described in Confalone et al., U.S. Pat. No. 3,978,084, the disclosure of which is incorporated herein by reference. An advantage that the process of this invention offers over the aforementioned Confalone et al. procedure is that there is no need to hydrogenate a thiophene moiety in order to obtain the biotin tetrahydrothiophene moiety. As can be seen from the earlier steps in this process, the tetrahydrothiophene moiety is present at a very early stage, thus obviating the attendant disadvantages of hydrogenation.

Compound XV may be converted to biotin by treatment with phosgene in the presence of an aqueous base. While any conventional aqueous base may be employed alkali metal carbonates are particularly preferred. This reaction can be carried out at atmospheric pressure and temperatures varying from about −20° C to about +75° C., preferably about 0° C.

The lactam of the formula XIV may alternatively be prepared by compound II undergoing a Michael addition to form a compound of the formula:

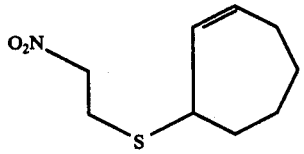

XVI.

Compound XVI is obtained by treating compound II with an alkali metal alkoxide and 1-nitro-2-acetoxyethane. This Michael addition is carried out at atmospheric pressure and at a temperature varying from about −20° C. to the reflux temperature of solvent employed, which is usually a lower alkanol, preferably absolute ethanol. This particular reaction generally affords a 99% yield of the Michael addition product, i.e., compound XVI.

Compound XVI is then converted to a compound of the formula

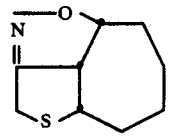

XVII by treatment of the former compound with a dehydrating agent, preferably arylisocyanates, most preferably phenyl isocyanate, in the presence of a catalytic amount of a nitrogen base. The preferred nitrogen bases are amines which may be selected from any of the bases mentioned hereinbefore. Triethylamine is particularly preferred. This reaction is carried out at atmospheric pressure and at a temperature of from about 25° C. to about 50° C. The reaction is generally carried out in a non-polar aromatic hydrocarbon solvent, e.g., benzene, toluene, or xylene. Compound XVII is particularly unique in that it possesses in its tricyclic system two of the three biotin stereocenters. Additionally, the reaction to form compound XVII is totally stereospecific thus paving the way for the formation of the biologically active stereoisomer of biotin.

Compound XVII is then reduced to form a compound having the formula:

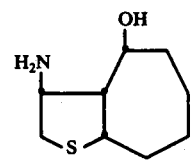

X

The compound of formula X is obtained from compound XVII by the same reduction procedure as that employed in the reduction of compound V to compound VI hereinbefore.

The compound of formula X may then be transformed to the compound of formula XIV by procedures set forth hereinbefore.

The compound of formula XIII, which is the immediate precursor to the lactam of formula XIV can be prepared alternatively when compound XI is a compound of the formula:

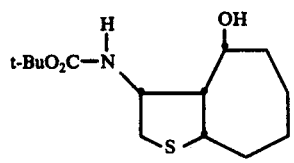

XIa

Compound XIa is then transformed successively to compounds

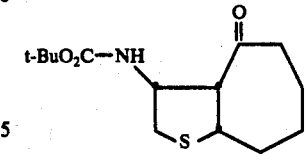

XIIa and

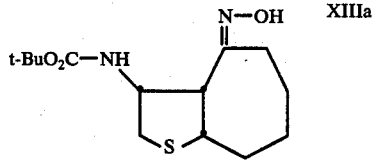

in accordance with the procedures set forth hereinbefore for the preparation of compounds XII and XIII.

Compounds XIIIa may then be treated with a strong acid, preferably trifluoroacetic acid, to form a compound of the formula:

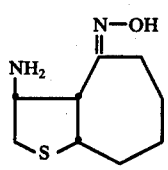

Compound XVIII may then be transformed to compound XIII by placing protecting groups onto the amino moiety of compound XVIII in the same manner as described hereinbefore with respect to forming compound XI from compound X.

The advantages of employing the carbo-t-butoxy protecting groups are survival of the protecting group moiety while the hydroxyl moiety of compound X is being transformed to an oxime and insurance that the acylation is limited to the nitrogen of the amino group to the exclusion of any acylation of the hydroxyl group. In addition, this particular protecting group is easily removable so that another nitrogen protecting group, which will survive the ensuing Beckmann rearrangement to compound XIV, may be utilized on compound XIII. This last advantage is important because the product yield in the Beckman rearrangement product is sensitive to the protecting group.

The non-limiting examples which follow are illustrative of this invention. All temperatures are in degrees Centigrade.

EXAMPLE 1

To a solution of 81.5 g (.466 mole) of 3-bromocycloheptene in 300 ml of acetonitrile cooled to 0° was added 13.13 ml (.466 mole) of thiolacetic acid. The system was treated dropwise with 64.55 ml (.466 mole) of triethylamine, during which time a precipitate of triethylamine hydrobromide separated. The cooling bath was removed and the reaction allowed to proceed at 25° for 2.0 additional hours. The reaction mixture was partitioned between IN HCl/methylene chloride. The aqueous phase was further extracted with methylene chloride. The organic extracts were pooled, dried over sodium sulfate, and evaporated. The residue was distilled in vacuo to afford 56.18 g (.330 mole, 71%), b.p. 64°–65°/.25mm of 3-acetylmercaptocycloheptene, as a colorless liquid.

EXAMPLE 2

A solution of fresh ethoxide prepared from 7.6 g (0.330 gram-atom metallic sodium) in 200 ml of absolute ethanol was treated dropwise with 56.18 g (0.330 mole) of 3-acetylmercaptocycloheptene in 10 ml of absolute ethanol. The reaction was heated under reflux for 15 minutes and then cooled to room temperature. A solution of 49.69 ml (.330 mole) of bromoacetaldehyde diethylacetal in 30 ml of absolute ethanol was added dropwise. The reaction mixture was heated under reflux for 2.0 hours and cooled. The precipitated sodium bromide was filtered and washed well with absolute ethanol. The filtrate was concentrated and the residue partitioned between ether/brine. The aqueous phase was further extracted with ether. The organic extracts were pooled, dried over magnesium sulfate, and evaporated to afford 80.1 g (.328 mole, 99%) of pure 3-[2,2-diethoxyethyl)thio]-1-cycloheptene, as a colorless oil.

EXAMPLE 3

A solution of 108.13 g (.433 mole) of 3-[2,2-diethoxyethyl)thio]-1-cycloheptene in 1000 ml of acetone/water, 9:1 was treated with 1.1 g of p-toluenesulfonic acid hydrate and heated under reflux for 1.0 hour, cooled, and concentrated. The residue was partitioned between ether/10% sodium bicarbonate. The aqueous phase was further extracted with ether. The organic extracts were pooled, dried over magnesium sulfate, and evaporated to afford 75.30 g (.443 mole, 100%) of 2-[(1-cyclohepten-3-yl)thio]acetaldehyde as a colorless oil.

EXAMPLE 4

A solution of 21.3 g (.125 mole) of 2-[(1-cyclohepten-3-yl)thio]acetaldehyde in 150 ml of acetonitrile was treated with 15.3 g (0.125 mole) of benzylhydroxylamine and 1 ml of triethylamine. The reaction was heated under reflux for 2.0 hours, cooled, and evaporated to dryness. The residue was triturated with benzene/ethyl acetate, 98:2, in which the product is soluble. An insoluble impurity was filtered off and the filtrate was concentrated and chromatographed over silica using the same solvent system for elution. The product was eluted after a less polar by-product was obtained as 22.80 g (.083 mole, 66%) of 2aβ, 4aβ,5,6,7,8,8aβ,8bβ-octahydro-2-benzyl-2H,3H-thieno[3',4',5':3,3a,4]cyclohept[d]-isoxazole as a pale yellow oil, which crystallized to a colorless solid. The product was recrystallized from petroleum ether to give an analytically pure sample, m.p. 56°–57° C.

EXAMPLE 5

To a suspension of 37.69 g (.137 mole) of 2aβ,-4aβ,5,6,7,8,8aβ,8bβ-octahydro-2-benzyl-2H,3H-thieno[3',4',5':3,3a,4]-cyclohept[d]-isoxazole in 400 ml of acetic acid/water, 1:1 was added 37.69 g (0.577 gram-atom) of zinc. The reaction was heated at 70° for 18 hours with efficient stirring and then cooled. The zinc salts were filtered off and the filtrate was concentrated. The residue was partitioned between 10% ammonium hydroxide/methylene chloride. The aqueous phase was further extracted, and the organic extracts were combined, dried over sodium sulfate, and evaporated to yield 36.28 g (.130 mole, 96%) of 2,3β,3aβ,5,6,7,8,8aβ,-octahydro-3α-benzylamino-4H-cyclopenta[b]-thiophen 4α-ol as a colorless oil.

EXAMPLE 6

A solution of 11.08 g (0.040 mole) of 2,3β,3aβ,5,6,7,8,8aβ-octahydro-3α-benzylamino-4H-cyclohepta[b]-thiophen 4α-ol in 200 ml of methanol and 100 ml of 10% sodium bicarbonate was treated with 6.79 ml (0.088 mole) of methyl chloroformate. After 2.0 hours of stirring, an additional 3.0 ml of methylchloroformate was added and the reaction was allowed to proceed for an additional hour. The mixture was partitioned between methylene chloride/water. The aqueous phase was further extracted with 3 × 200 ml of methylene chloride. The organic extracts were pooled, dried over sodium sulfate, and evaporated to yield 15.65 g (.040 mol, 100%) of benzyl[2,3β,3a62 , 5,6,7,8,8aβ-octahydro-4α-methoxycarbonyl-4H-cyclohepta[b]thiophen-3α-yl]carbamic acid, methyl ester as a colorless oil.

EXAMPLE 7

A solution of 23.0 g (.058 mole) of benzyl 2,3 3aβ,5,6,7,8,8aβ-octahydro-4α-methoxycarbonyl-4H-cyclohepta [b]-thiophen-3αyl-carbamic acid, methyl ester in 150 ml of methanol was treated with 75 ml of 1N sodium hydroxide and heated under reflux for 18.0 hours. The reaction mixture was cooled and partitioned between methylene chloride/water. The aqueous phase was further extracted. The organic extracts were pooled, dried over sodium sulfate, and evaporated to give 18.0 g (.058 mole, 100%) of 3aβ,5aβ,9bβ-2H-thieno[3,4,5-de]-cyclohepta[1,3]-oxazin-2-one, decahydro-3-benzyl as a crystalline solid. The product was recrystallized from methanol to afford the analytical sample, m.p. 153°–154°.

EXAMPLE 8

A solution of 8.0 g (26.4 mmoles) of 3aβ,5aβ,9aβ,9bβ-2H-thieno[3,4,5-de]-cyclohepta[1,3]oxazin-2-one, decahydro-3-benzyl in 100 ml of dry tetrahydrofuran was added to 400 ml of liquid ammonia cooled to −78° C. To this solution, 3.0 g (0.130 gram-atom) of metallic sodium was added in small portions over 0.5 hour. Reaction was allowed to proceed until the blue color disappeared at which point 5.0 g of ammonia chloride was added. The cooling bath was removed and the ammonia was allowed to evaporate overnight at 25°. The residue was partitioned between 1N HCl/methylene chloride. The aqueous phase was further extracted with methylene chloride. The organic extracts were pooled, dried over sodium sulfate, and evaporated to dryness to yield 5.0 g (23.4 mmoles), 89%) of pure 3aβ,5aβ,9aβ,9bβ-2H-thieno[3,4,5-de]cyclohepta-[1,3]oxazin-2-one, decahydro as a crystalline solid. After recrystallization from ethyl acetate, the analytical sample melted at 197°–198°.

EXAMPLE 9

A suspension of 5.0 1 g (23.4 mmoles) of 3aβ,5aβ,9aβ,9bβ-2H-thieno[3,4,5-de]cyclohepta[1,3]oxazin-2-one, decahydro in 50 ml of 2N sodium hydroxide was heated under reflux for 16.0 hours and cooled. The reaction mixture was partitioned between methylene chloride/1N HCl. The aqueous phase was further extracted with methylene chloride and the organic extracts were discarded. The pH of the aqueous phase was adjusted to 10 by the addition of concentrated ammonium hydroxide. The aqueous phase was now further extracted with 4x 100 ml portions of methylene chloride. The organic extracts were pooled, dried over sodium sulfate, and evaporated to yield 2.78 g (14.9 mmoles, 64%) of 2,3β,3aβ,5,6,7,8aβ-octahydro-3α-amino4H-cyclohepta-[b]-thieno-4α-ol as a colorless oil.

EXAMPLE 10

A solution of 3.0 g (16 mmoles) of 2,3β,3aβ,5,6,7,8-,8aβ-octahydro-3α-amino-4H-cyclohepta[b]thiophen-4α-ol in 80 ml of methanol was treated with 32 ml of 10% sodium bicarbonate. To the milky solution was added 1.8 ml (16 mmoles) of methylchloroformate. The reaction was allowed to proceed for 0.5 hours and then was partitioned between methylene chloride/water. The aqueous phase was further extracted. The organic extracts were pooled, dried over sodium sulfate, and evaporated to yield, 3.70 g (15.1 mmoles, 94%) of 2,3β,3aβ,5,6,7,8 aβ-octahydro-4α-hydroxy-4H-cyclohepta[b]thiophen-3α-yl-carbamic acid, methyl ester as a crystalline solid. An analytical sample, m.p. 109–110°, was prepared by recrystallizing 2,3β,3aβ,5,6,7,8aβ-octahydro-4α-hydroxy-4H-cyclohepta[b]-thiophen-3α-yl-carbamic acid, methyl ester from ethyl acetate/petroleum ether.

EXAMPLE 11

Following the procedure of Example 10 but employing p-toluene sulfonyl chloride instead of methylchloroformate there was obtained 2,3β,3aβ,5,6,7,7aβ-octahydro-4α-hydroxy-3α-[[(4-methylphenyl)sulfonyl]amino]-4H-cyclohepta[b] thiophene, m.p. 166°–167°. An analytical sample was prepared by recrystallization from ethanol.

EXAMPLE 12

Following the procedure of Example 10 but employing acetic anhydride instead of methylchloroformate there was obtained 2,3β,3aβ,4β,5,6,7,7aβoctahydro-4α-hydroxy-3α-acetamido-4H-cyclohepta[b]thiophene, m.p. 146°–147°. An analytical sample was prepared by by recrystallization from ethyl acetate.

EXAMPLE 13

Following the procedure of Example 10 but employing t-butoxycarbonyl azide instead of methylchloroformate there was obtained 2,3β,3aβ,5,6,7,8,8aβ-octahydro-4α-hydroxy-4H-cylcohepta[b]thiophen-3α-yl-carbamic acid, t-butyl ester, m.p. 113°–114°. An analytical sample was prepared by recrystallization from hexane.

EXAMPLE 14

A solution of 2.4 g (9.78 mmoles) of 2,3β,3aβ,5,6,7,8,-8aβ-octahydro-4α-hydroxy-4H-cyclohepta[b]thiophen 3α-yl-carbamic acid, methyl ester in 45 ml of dimethylsulfoxide was treated with 30 ml of acetic anhydride. The reaction was allowed to proceed overnight. The solvents were removed in vacuo at the pump to yield 2.4 g (9.77 mmoles, 100%) of pure 2,3β,3aβ,5,6,7,8, 8aβ-octahydro-4-oxo-4H-cyclohepta[b]thiophen-3α-yl-carbamic acid, methyl ester as a crystalline solid. An analytical sample, m.p. 102°–103°, was prepared by recrystallizing from ethyl acetate/petroleum ether.

EXAMPLE 15

Following the procedure of Example 14, the compound of Example 11 was converted to 2,3β,3aβ,5,6,8,-8aβ-octahydro-3α-[[(4-methylphenyl)-sulfonyl]amino]-4H-cyclohepta[b]thiophene-4-one, m.p. 142°–143°. An analytical sample was prepared by recrystallization from ethanol.

EXAMPLE 16

Following the procedure of Example 14, the compound of Example 12 was converted to 2,3β,3aβ,5,6,7,8,8aβ-octahydro-3α-acetamido-4-oxo-4H-cyclohepta[b]-thiophen-3α-yl-carbamic acid, t-butyl ester, m.p. 116°–117°. An analytical sample was prepared by recrystallization from ethyl acetate.

EXAMPLE 17

Following the procedure of Example 14, the compound of Example 13 was converted to 2,3β,3aβ,5,6,7,8,8aβ-octahydro-4-oxo-4-H-cyclohepta[b] thiophene, m.p. 152°-153°. An analytical sample was prepared by recrystallization from ethyl acetate/petroluem ether.

EXAMPLE 18

A solution of 183 mg (.753 mmole) of 2,3β,3aβ,5,6,7,8,8aβ-octahydro-4-oxo-4H-cyclohepta[b]thiophen-3α-yl-carbamic acid, metyl ester in 5 ml of ethanol and 0.2 ml of pyridine was treated with 69 mg (1.0 mmole) of hydroxylamine hydrochloride. The reaction was heated under reflux for 0.5 hours and cooled. The mixture was partitioned between methylene chloride/1N HCl. The aqueous phase was further extracted. The organic extracts were combined, dried over sodium sulfate, and evaporated to yield 173 mg (.670 mmole, 89%) of pure 2,3β,3aβ,5,6,7,8,8aβ-octahydro-4-hydroxyimino-4H-cyclohepta[b]thiophen-3α-yl-carbamic acid methyl ester as a crystalline solid. An analytical sample, m.p. 123°-124°was prepared by recrystallizing from ethyl acetate/pentane.

EXAMPLE 19

Following the procedure of Example 18, the compound of Example 15 was converted to 2,3β,3aβ,5,6,7,8,8aβ-octahydro-3α-[[(4-methylphenyl)-sulfonyl]amino]-4H-cyclohepta[b]thiophen-4-one, antioxime, m.p. 181°-182°. An analytical sample was recrystallized from ethanol.

EXAMPLE 20

Following the procedure of Example 18, the compound of Example 16 was converted to 2,3β,3aβ,5,6,7,8,8aβ-octahydro-3α-acetamido-4-oxo-4H-cyclohepta[b]thiophene, antioxime, m.p. 213°-214° (ethyl acetate). An analytical sample was recrystallized from ethyl acetate.

EXAMPLE 21

Following the procedure of Example 18, the compound of Example 17 was converted to 2,3β,3aβ,5,6,7,8,8aβ-octahydro-4-hydroxy-imino-4H-cyclopheta[b]thiophen-3α-yl-carbamic acid, t-butyl ester, m.p. 167°-168° (ethyl acetate/hexane). An analytical sample was recrystallized from ethyl acetate/hexane.

EXAMPLE 22

A mixture of 350 mg (1.35 mmoles) of 2,3β,3aβ,5,6,7,8,8aβ-octahydro-4-hydroxyamino-4H-cyclohepta[b]thiophen-3α-yl-carbamic acid, methyl ester in 10.0 g of polyphosphoric acid was mechanically stirred at 100° for 15.0 minutes. The reaction mixture was hydrolyzed by ice water and then partitioned between brine/methylene chloride:methanol, 9:1. The aqueous phase was further extracted with methylene chloride/methanol, 9:1. The organic extracts were pooled, dried over sodium sulfate, and evaporated to leave a 160 mg residue. This material was chromatographed on 2 thick layer silica plates using ethyl acetate as the eluent. The product, 3-amino-4[N-carbomethoxyamino]tetrahydro-2-thiophenevaleric acid lactam was isolated at $R_f$ = 0.2 and was obtained as 69 mg (0.27 mmole, 20%) of a crystalline solid which recrystallized from ethyl acetate and melted at 242°-243°.

EXAMPLE 23

A solution of 50 mg. (.14 mmole) of 2,3β,3aβ5,6,7,8,-8aβ-octahydro-3α-[[(4-methylphenyl)sulfonyl]amino]-4H-cyclohepta[b]thiophen-4-one, antioxime in 3.7 g of polyphosphoric acid (PPA) was mechanically stirred at 50° for 8.0 hours. The PPA was hydrolyzed and the product mixture was extracted with methylene chloride/methanol 4:1. The organic extracts were combined, dried over sodium sulfate, and evaporated to yield 30 mg of residue. The material was chromatographed on thick layer silica plates using ethyl acetate as the eluent. The product was isolated at $R_f$ = 0.4 and amounted to 15 mg. (30%) of pure all cis-4-p-toluene sulfonamido-3-aminotetrahydrothiophen-2-valeric acid lactam, m.p. 210° (dec).

EXAMPLE 24

A suspension of 90 mg (0.349 mmole) of 3-amino-4-N-carbomethoxyamino tetrahydro-2-thiophenevaleric acid lactam in 15 ml of water was treated under argon with 3.0 g of barium hydroxide monohydrate. The reaction mixture was heated under reflux for 20 hours, cooled, and the barium salts were filtered off and washed with water. The filtrate was concentrated, cooled to 0° and treated with gaseous phosgene until the solution was acidic to congo red. The reaction was allowed to stand for 1.5 hours at 25° and then was evaporated to dryness. This residue, which is mixture of biotin and inorganic salts, is taken up in 15 ml of dry methanol and treated with two drops of concentrated sulfuric acid. The mixture is heated under reflux for 1.5 hours and then cooled to 25°. The inorganic salts are filtered off and washed with chloroform/methanol, 4:1. The filtrate was partitioned between water/chloroform: methanol, 4:1. The aqueous phase was further extracted with chloroform/methanol, 4:1. The organic extracts were combined, dried over sodium sulfate and evaporated to yield 45 mg (0.174 mmole, 50%) of pure biotin methyl ester, m.p. 132°-133°, after recrystallization from ethyl acetate. The conversion of biotin methyl ester to biotin was accomplished according to the procedure of V. du Vigneaud[1]./

[1]. V. du Vigneaud, K, Hofmann, D. B. Melville, and J. R. Rachele, *J. Biol. Chem.*, 140, 763 (1941).

EXAMPLE 25

To 40 ml of absolute ethanol was added 1.38 g (.060 gram atom) metallic sodium. When the reaction was completed 10.2 g ( b .060 mole) of 3-acetylmercaptocycloheptane in 20 ml of absolute ethanol was added and the reaction mixture was brought up to reflux for 15 minutes. The solution was then cooled to 0° and 7.98 g (.060 mole) of 1-nitro-2-acetoxyethane in 20 ml absolute ethanol was added. The reaction was allowed to proceed for 3.0 hours at 0° and then was partitioned between 1N HCl and methylene chloride. The aqueous phase was further extracted with methylene chloride. The organic phases were pooled, dried over sodium sulfate, and evaporated to afford 12 g (99%) of pure 3-[2-nitroethylthio]cycloheptene as a colorless oil.

EXAMPLE 26

A solution of 15.2 g (0.075 mole) 3-[2-nitroethylthio]-cycloheptene in 200 ml of dry benzene was treated with 24 ml (0.224 mole) of phenylisocyanate and 0.5 ml of triethylamine. The mixture was stirred 24 hours at room temperature. The white solid (carbanilide) which had separated was filtered off and washed well with benzene. The filtrate was evaporated to dryness and residue was chromatographed over one kg. silica eluting with benzene/ethyl acetate (98:2). Fractions containing the product were combined and evaporated to afford 10.8 g (0.060 mole, 79%) of pure 3,4a$\beta$,5,6,7,8,9$\beta$,9a$\beta$-octahydrocycloheptano [b 5,5a, 6-f,g]-thieno(3,4-c)isoxazole as a colorless oil.

EXAMPLE 27

A solution of 3.66 g (0.020 mole) of 3,4a$\beta$, 5,6,7,8,9$\beta$,9a$\beta$-octahydrocycloheptane[5,5a,6-f,g]thieno[3,4-c]isoxazole in 150 ml of anhydrous ether was added dropwise at 25° (water bath) under argon to 1.64 g (0.043 mole) lithium aluminum hydride suspended in 50 ml of anhydrous ether. The mixture was refluxed for 4.0 hours, cooled, and quenched dropwise with 50 ml. concentrated sodium sulfate. The reaction was extracted four times with ether. Th organic extracts were combined, dried over sodium sulfate, and evaporated to yield 3.43 g (0.018 mole, 92%) of 2,3$\beta$,3a$\beta$,5,6,7,8,8a$\beta$-octahydro-3$\alpha$-amino-4H-cyclohepta [b]-thiophen-4$\alpha$-ol as a colorless oil. For characterization , the compound was converted to its hydrochloride salt by methanolic hydrogen chloride to afford a pure sample of 2,3$\beta$,3a$\beta$,5,6,7,8,a$\beta$-octahydro-3$\beta$-amino-4H-cyclohepta[b]thiophen-4$\beta$-ol, hydrochloride, m.p. 191°-193°. Recrystallization from ethanol/ether yielded an analytical sample, m.p. 192-193°.

EXAMPLE 28

A solution of 3.9 g (0.010 mole) of 2,3$\beta$,3a$\beta$,5,6,7,8-,8a$\beta$-octahydro-4-hydroxyimino -4H-cyclohepta [b]thiophen carbamic acid, t-butyl ester in 10 ml of trifluoracetic acid was stirred at 0° for 1.5 hours. The solvent was evaporated and the residue was recrystallized from methanol-ether to yield 2.3 g (.0073 mole, 73%) of pure 2,3$\beta$,3a$\beta$,5,6,7,8, 8a$\beta$-octahydro-3$\alpha$-amino-4-(4H cyclohepta [b]thiophene antioxime trifluoroacetae m.p. 180°-181° , as a fluffy white solid.

EXAMPLE 29

A solution of .628 g (.002 mole) of 2,3$\beta$,3a$\beta$,5,6,7,-8,a$\beta$-octohydro-3$\beta$amino-4-(4H)-cyclohepta[b]thiophene, antioxime trifluoroacetate acid anhydride. The solution was stirred at 25° for 15 minutes and then partitioned between IN HCl/methylene chloride. The aqueous phase was further extracted with methylene chloride. The organic phases were combined, dried over sodium sulfate, and evaporated to yield 0.590 g (.002 mole, 100%) of pure 2,3$\beta$,3a$\beta$, 5,6,7,8,8a$\beta$-octahydro-3$\alpha$-trifluoroacetamido-4-oxo-4H-cyclohepta[b]thiophene, antioxime, m.p. 213°-214°. The compound may be recrystallized from ethyl actate.

We claim:

1. A compound of the formula

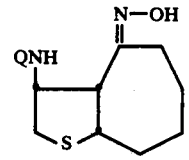

wherein Q is —CO$_2$R$_4$, where R$_4$ is lower alkyl the racemates and optical antipodes thereof.

2. The compound of claim 1 wherein Q is

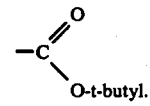

3. The compound of claim 1 wherein Q is

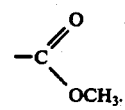

* * * * *